United States Patent
Åkerfeldt et al.

(10) Patent No.: US 7,637,921 B2
(45) Date of Patent: Dec. 29, 2009

(54) FEMORAL COMPRESSION DEVICE WITH PROGRESSIVE PRESSURE DEVICE

(75) Inventors: Dan Åkerfeldt, Uppsala (SE); Per Egnelöv, Uppsala (SE); Lars Tenerz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 591 days.

(21) Appl. No.: 10/378,078

(22) Filed: Mar. 4, 2003

(65) Prior Publication Data

US 2004/0176796 A1 Sep. 9, 2004

(51) Int. Cl.
*A61B 17/00* (2006.01)
*A61M 29/00* (2006.01)
(52) U.S. Cl. .................... 606/201; 606/202
(58) Field of Classification Search .............. 606/201, 606/202, 191
See application file for complete search history.

(56) References Cited

U.S. PATENT DOCUMENTS

| | | | | |
|---|---|---|---|---|
| 5,307,811 A | * | 5/1994 | Sigwart et al. | 600/490 |
| 5,542,427 A | | 8/1996 | Åkerfeldt | |
| 5,968,072 A | * | 10/1999 | Hite et al. | 606/202 |
| 5,997,564 A | * | 12/1999 | Shehata et al. | 606/201 |
| 6,503,266 B1 | | 1/2003 | Sjögren et al. | |
| 6,592,533 B1 | * | 7/2003 | Yonekawa et al. | 601/148 |
| 2003/0028214 A1 | * | 2/2003 | Benz et al. | 606/201 |

FOREIGN PATENT DOCUMENTS

| | | |
|---|---|---|
| EP | 0 462 088 B1 | 11/1995 |
| JP | 5-305093 A | 11/1993 |
| WO | WO 94/05221 A1 | 3/1994 |
| WO | WO 98/34547 A1 | 8/1998 |

OTHER PUBLICATIONS

U.S. Appl. No. 10/235,859, filed Sep. 6, 2002, Åkerfeldt.
U.S. Appl. No. 10/209,974, filed Aug. 2, 2002, Åkerfeldt.
U.S. Appl. No. 10/322,809, filed Dec. 19, 2002, Åkerfeldt et al.

* cited by examiner

*Primary Examiner*—Vy Q Bui
(74) *Attorney, Agent, or Firm*—Foley & Lardner LLP

(57) ABSTRACT

A femoral compression device (1; 41; 51; 61) for compressing a femoral artery of a patient is provided. The femoral compression device (1; 41; 51; 61) comprises a pressure device (7; 21; 31; 42; 55; 62), a compression member (8; 43; 56; 65) for compressive bearing against a puncture site, a base portion (3; 44; 52) provided with two opposing extensions (4, 5; 45, 46; 53, 54), to the ends of which a belt (6), which is adapted to be arranged around the patient's body, can be fixed. According to the invention, the pressure device (7; 21; 31; 42; 55; 62) is characterized by non-uniform overall action constants, such that when a low compression pressure is applied, the pressure device (7; 21; 31; 42; 55; 62) exhibits a small action constant, and when a high compression pressure is applied, the pressure device (7; 21; 31; 42; 55; 62) exhibits a large action constant.

6 Claims, 2 Drawing Sheets

FEMORAL COMPRESSION DEVICE WITH PROGRESSIVE PRESSURE DEVICE

FIELD OF THE INVENTION

The present invention relates generally to a femoral compression device comprising a pressure device that provides the pressure for compressing a femoral artery of a patient, and more particularly to a femoral compression device comprising a pressure device being characterized by having a non-uniform action over its operating range.

BACKGROUND OF THE INVENTION

The present invention is a modification of the femoral compression devices disclosed in the patents U.S. Pat. No. 5,307,811 and EP 0 462 088 B1, which are assigned to the present assignee and which claim priority from SE 9002077 and SE 9003271. A femoral compression device according to these publications comprises basically a pressure device for compressive bearing against a puncture site at a femoral artery of a patient (the puncture being made to access the patient's vascular system for various procedures), a belt adapted to be fixed around the patient's body, and a base plate supporting the pressure device and being provided with two extensions. The pressure device according to these publications is a pneumatic device in the form of an inflatable air cushion or balloon, different embodiments of which have also been disclosed in U.S. Pat. No. 5,542,427, WO 94/05221, WO 98/34547 and U.S. application Ser. Nos. 09/355,736, 10/209,974 and 10/235,859, which all are assigned to the present assignee. In U.S. application Ser. No. 10/322,809, which also is assigned to the present assignee, the pressure device is instead in the form of a coil spring, which is connected to a compression member being adapted for compressive bearing against a puncture site at a femoral artery. All of the documents cited in this paragraph are incorporated herein by reference.

During use of a femoral compression device according to the publications mentioned above, the inflatable air cushion or compression member is positioned over a femoral artery of a patient, and the belt, which extends from the end of the first extension, around the patient's body and to the end of the second extension, is tightened. Then, the pressure device is actuated to thereby apply compression pressure such that the femoral artery is compressed in order to prevent bleeding through a puncture hole being made in the artery wall. Usually, the compression procedure involves a short initial compression (for 1-5 minutes) at a relatively high pressure (usually above the systolic pressure) followed by a longer post-compression (for 3-120 minutes) at a lower pressure (usually below the diastolic pressure). Consequently, a femoral compression device and its accompanying pressure device must be able to operate within a fairly large pressure range, going from about 30 mmHg to about 250 mmHg. Because of this large operating range and for reasons to be discussed below, the pressure device of the known femoral compression devices can be improved.

SUMMARY OF THE INVENTION

For the sake of clarity, the description of the present invention will be mainly directed to a pressure device in the form of a mechanical device, such as one or several coil springs or other types of springs, but it should be understood that the principles according to the invention are equally applicable to a pressure device in the form of a pneumatic means, such as an inflatable air cushion or balloon, or a combination of mechanical and pneumatic pressurizing component(s), or other types of pressure devices.

A common feature of the pressure device according to the publications listed above—whether it is in the form of a pneumatic device or in the form of a mechanical, spring-type device—is that the pressure device, at least within its main operating range, can be characterized by a single action constant. For a pressure device in the form of a coil spring this action constant is the so-called spring constant, which, according to Hook's law, gives the force required to compress the spring a certain distance or, equivalently, the force exerted by the coil spring for a given compression.

As indicated above, especially the post-compression period can be rather lengthy, and during this post-compression period it frequently happens that the patient moves. Such movements, either they are intentional or unintentional, will more or less unavoidably lead to a change in the compression length of the pressure device and therefore to a change in the compression pressure applied, which, in turn, can lead to unnecessary bleeding.

In this respect, a femoral compression device should therefore be "forgiving" regarding movements of the patient, i.e. the compression pressure should not change drastically for small changes in the compression of the pressure device in question. For a pressure device in the form of a coil spring, a perhaps natural way to address this problem would be to use a coil spring having a small spring constant. However, to use a coil spring characterized by a small spring constant implies that a rather long coil spring has to be provided, in order to be able to apply the necessary large compression pressure required especially during the initial compression phase. The use of such a long coil spring entails at least two disadvantages: (1) a long regulating range of the actuation means that adjusts the compression length of the coil spring, and (2) a large construction space has to be provided to accommodate the coil spring.

If the actuation means is in the form of a handle which a user turns to compress the coil spring, the first disadvantage implies that the handle has to be rotated several turns before the required large initial compression pressure is applied on the femoral artery. Having in mind that the bleeding from the femoral artery usually is quite severe, an adjustment that takes an unduly long time is a significant disadvantage that may lead to unnecessary bleeding.

Especially if the coil spring is arranged essentially perpendicular to the base plate of the femoral compression device, the second disadvantage implies that the femoral compression device is rendered a design that occupies a lot of storing space and which is also awkward to use. And even if the coil spring is accommodated in a recess within one of the two extensions of the femoral compression device, such a long recess may weaken the overall strength of the femoral compression device and may also lead to difficulties in the manufacturing of the femoral compression device.

The object of the present invention is therefore to provide a femoral compression device being provided with a pressuring device that allows movements by the patient without leading to a drastic change in the compression pressure applied on the femoral artery. At the same time, the pressure device should allow a short regulating range for the actuation means that regulate the compression pressure, so that a quick adjustment can be achieved. Further, the adjusting means should not occupy an excessive amount of the available construction space.

The above-mentioned object is achieved by a femoral compression device which is provided with a pressure device being characterized by a non-uniform action, such that a large action constant is provided when a high compression pressure is required and a small action constant is provided when a low compression pressure is required. In a first embodiment of the present invention, the pressure device is provided in the form of at least two coil springs having different spring constants. In the first embodiment, the coil springs are arranged such that the coil springs essentially operate in sequence, whereas a second embodiment discloses an arrangement where at least two coil springs operate concurrently. In a third embodiment, the pressure device is in the form of a single coil spring, which is characterized by having at least two portions with different spiral pitches and thereby different spring constants. In a fourth embodiment of the present invention, the pressure device is in the form of a leaf spring, the active length of which can adjusted and which has such a shape that different spring constants are obtained for different active lengths. A fifth embodiment discloses a combination of a mechanical pressurizing means and a pneumatic pressurizing means.

DESCRIPTION OF THE PREFERRED EMBODIMENTS

Figure 1:
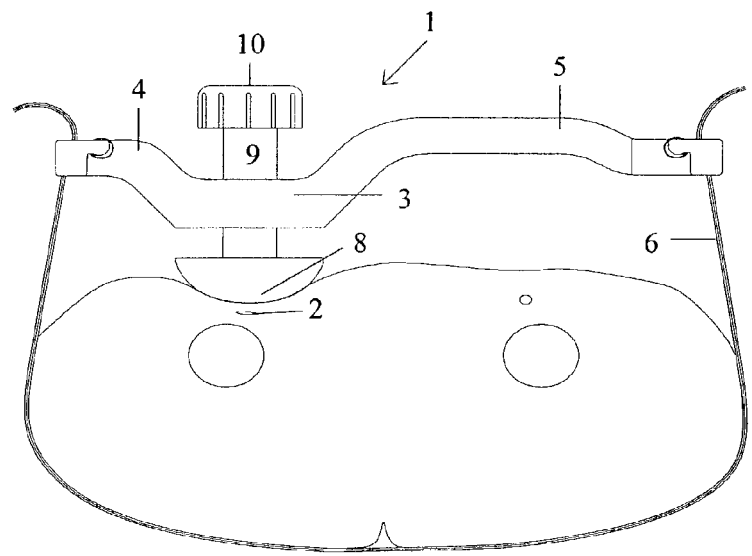
FIG. 1 is a schematic cross-sectional view of a femoral compression device according to the present invention which is attached to the body of a patient.

FIG. 1 illustrates schematically how a femoral compression device 1 according to the present invention is attached to the body of a patient in order to apply compression pressure on a femoral artery 2 in which a puncture hole has been made. The femoral compression device 1 comprises basically a base plate 3 provided with two opposing extensions 4 and 5, to the ends of which a belt 6, which is arranged around the patient's body, is fixed. The femoral compression device 1 comprises further a pressure device 7 (not shown in the figure), which is connected to a compression member 8 being adapted for compressive bearing against the puncture site. The pressure device 7 is accommodated in a housing 9 and can be actuated by a knob or handle 10.

Figure 2:
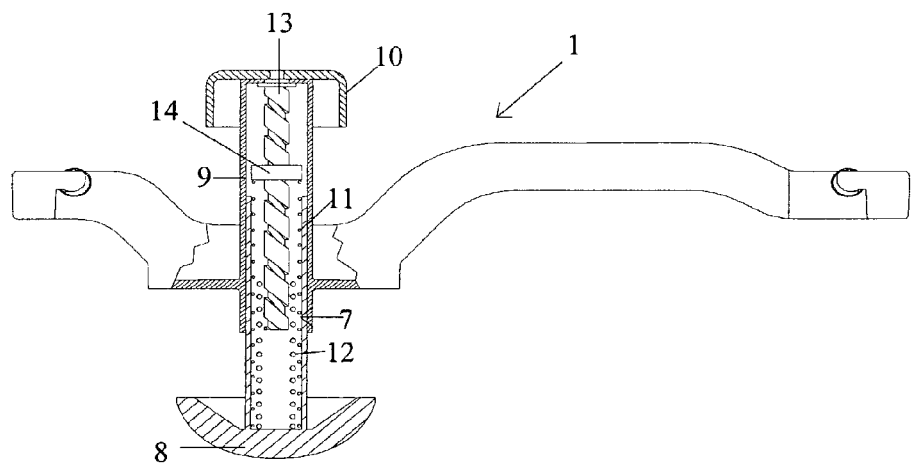
FIG. 2 is a cross-sectional view of the pressure device of the femoral compression device of FIG. 1 in a first state.

FIG. 2 is a cross-section of the pressure device 7 of the compression device 1 illustrated in FIG. 1. Although somewhat difficult to discern from FIG. 2, the pressure device 7 is in this first embodiment of the present invention in the form of two coil springs 11 and 12. The first coil spring 11 has a first length and is characterized by a first spring constant, while the second coil spring 12 has a second length and is characterized by a second spring constant. In this specific embodiment, the first length is longer than the second length and the first spring constant is smaller than the second spring constant. The first and second coil springs 11, 12 are arranged such that the respective lower ends of the first and second coil springs 11, 12 are attached to the compression member 8, with the second coil spring 12 being positioned inside the first coil spring 11. An adjusting screw 13, whose upper end is connected to the handle 10, is threaded through an internally-threaded washer 14, which bears against the upper end of the first coil spring 11. The washer 14 can slide within housing 9 but is prevented from turning within the housing 9.

Herein, the terms "small" and "large" spring constants, respectively, refer to how easy a spring being characterized by a certain spring constant is compressed. A small spring constant implies that the spring is relatively easily compressed, or that the spring for a certain compression exerts only a relatively small amount of force. A large spring constant, on the other hand, implies that a relatively large amount of force is required to compress the spring, or that the spring for a certain compression exerts a relatively large amount of force. In practise, suitable specific values for the spring constants can be determined from tests or calculations, and can also be tailored to different fields of application, such as different body constitutions of the patients on which a femoral compression device is to be attached. The corresponding definitions also apply for the more general terms "small" and "large" action constants, respectively.

In FIG. 2, the pressure device 7 is shown in a state where the washer 14 presses only against the first coil spring 11, which is only slightly compressed. Since there is no force acting on the second coil spring 12, the second coil spring 12 is completely uncompressed and the overall action of the pressure device 7 is given by the first coil spring 11 only. If the first spring constant is relatively small, this state would therefore correspond to a situation in which only a small amount of compression pressure is applied on a femoral artery, which according to the above would be during the post-compression phase of the compression treatment of a patient.

Figure 3:
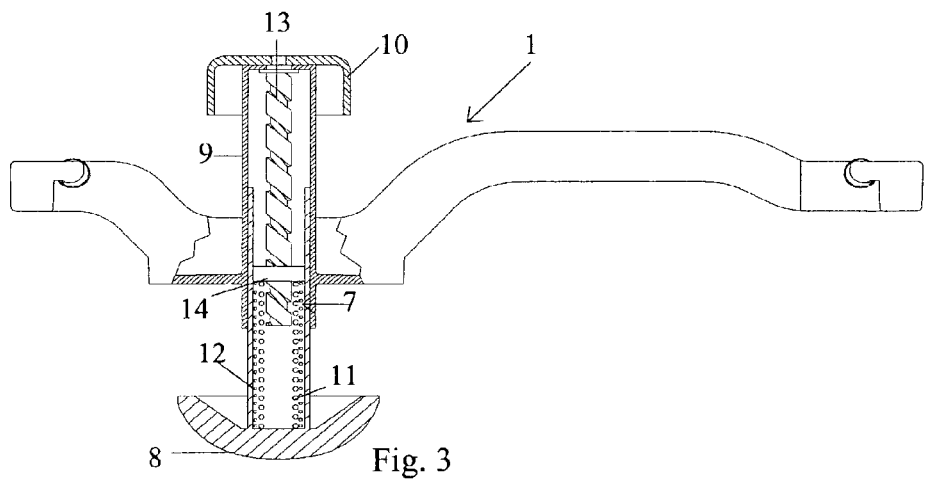
FIG. 3 is a cross-sectional view of the pressure device of FIG. 1 in a second state.

To apply more compression pressure—as is required during the initial compression phase—the handle 10 is turned, which causes the washer 14 to move downwards along the threads of the adjusting screw 13. In the position shown in FIG. 3, the washer 14 compresses both the first coil spring 11 and the second coil spring 12. Consequently, the overall action constant now larger, and this state would therefore correspond to a situation in which a rather large amount of compression pressure is applied on a femoral artery.

In the first embodiment of a pressure device according to the present invention, the coil springs 11, 12 have been arranged such that for a low compression pressure the action of the femoral compression device 1 is governed by the first coil spring 11 only, while for a higher compression pressure the action is mainly determined by the second coil spring 12, which has the larger spring constant. There are many ways to arrange two (or more) coil springs. The coil springs could, for example, be arranged side by side, or the coil springs could be accommodated in one or both of the extensions. The coils springs could be actuated by a common actuation means, such as the handle 10 shown in FIGS. 2 and 3, or more actuation means could be provided, with each actuation means being connected to a single coil spring.

Figure 4:
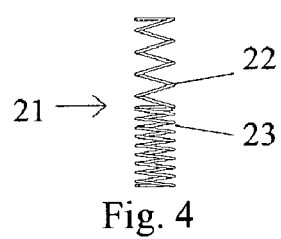
FIG. 4 illustrates a second embodiment of a pressure device according to the present invention.

A principally somewhat different way of obtaining a non-uniform overall action for the pressure device is illustrated in FIG. 4, where a second embodiment of a pressure device 21 comprises a first coil spring 22 being characterized by a first spring constant and a second coil spring 23 being characterized by a second spring constant. In this embodiment, one end of the first coil spring 22 is connected to one end of the second coil spring 23. With this arrangement, the overall action of the pressure device 21 is governed by both the first and second spring constants throughout the whole operating range of the pressure device 21.

Figure 5:
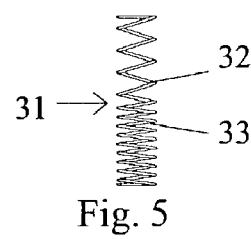
FIG. 5 illustrates a third embodiment of a pressure device according to the present invention.

A third embodiment of a pressure device 31 is illustrated in FIG. 5. In this embodiment, the pressure device 31 consists of a single coil spring 31, which has two portions, a first portion 32 and a second portion 33. As can be seen in the figure, the first and second portions 32, 33 have different spring pitches, which, in turn, implies that the first and second portions 32, 33 are characterized by different spring constants. The overall action of the pressure device 31 illustrated in FIG. 5 is therefore essentially the same as the action obtained by the pressure device 21 illustrated in FIG. 4. The same effect could also be achieved by a coil spring having two coil portions with different stiffness, which could be obtained by different coil thicknesses or different materials in the different portions. In particular from FIG. 4 and FIG. 5 it should be apparent that three or more coil springs could be provided after each other, or that a single coil spring having more than two portions with different spring constants could be provided, or any combination thereof.

Figure 6:
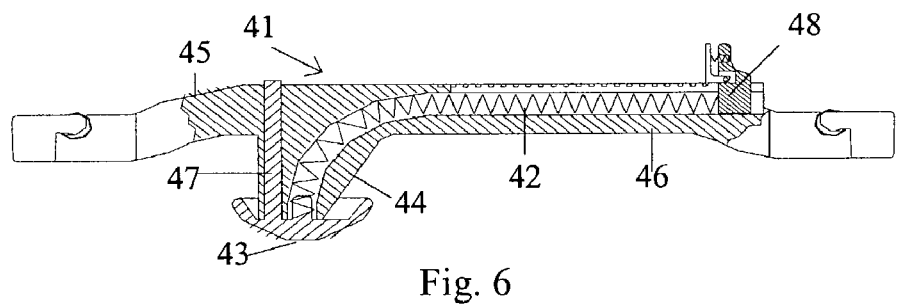
FIG. 6 illustrates an alternative arrangement of a pressure device according to the present invention within a femoral compression device.

As mentioned above, a pressure device in the form of one or several coil springs could be accommodated in one of the extensions provided on the base plate of a femoral compression device. In FIG. 6 such an arrangement is illustrated, where a compression device 41 comprises a pressure device 42 in the form of a coil spring 42 of, for example, the type illustrated in FIG. 5, i.e. the coil spring 42 has two portions with different spring pitches and thereby different spring constants. The coil spring 42 is connected to a compression member 43 being adapted for bearing against a puncture site, and a base portion 44, which is provided with two opposing extensions 45 and 46, to which a belt (not shown in the figure) can be attached. The coil spring 42 is partly arranged in one of the two extensions 46 and partly in the base portion 44. This arrangement of the coil spring 42 makes efficient use of the available space within the extension 46 and base portion 44. A handle 48 is provided at the extension 46 in which the spring coil 42 is arranged, and is connected to the first end of the coil spring 42, the second end of which is connected to the compression member 43. The handle 48, which is variable along the extension 46, is provided with a locking mechanism, so that the handle 48 can be moved, against the action of the coil spring 42, and be locked in any one of many possible positions along the extension 46. Alternatively, the handle can be designed such that the handle is infinitely variable along the extension (that is, the handle can be locked in an infinite number of positions). The compression member 43 is further provided with a guide rod 47, which is slidable within a guide hole provided inside the base portion 44. The purpose of the guide rod 47 and the corresponding guide hole is to provide a stable and reliable movement of the compression member 43. The guide rod 47 and the guide hole can preferably have non-cylindrical cross-sections, which prevents the guide rod 47 from rotating inside the guide hole.

Figure 7:
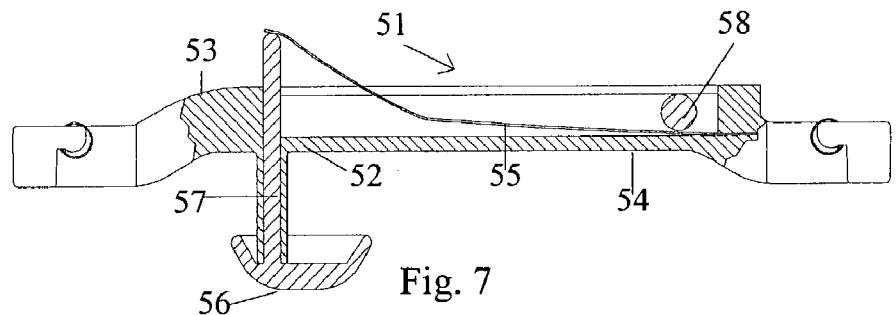
FIG. 7 illustrates a fourth embodiment of a pressure device according to the present invention.

FIG. 7 shows a fourth embodiment of a pressure device according to the present invention. Here, a femoral compression device 51 comprises basically a base portion 52 provided with two opposing extensions 53, 54, a pressure device 55 and a compression member 56 provided with a rod 57, which is connected to the pressure device 55. In this embodiment, the pressure device 55 is in the form of a leaf spring 55 and is partly accommodated within a recess in one of the extensions 54. By moving a handle 58, a user can adjust the active length of the leaf spring 55, such that the compression pressure exerted by the compression member 56 on a puncture site at a femoral artery can be controlled. As is seen in the figure, the leaf spring 55 is curved, with a non-uniform curvature. The leaf spring 55 will therefore exhibit a non-uniform spring constant, with a comparatively larger spring constant for a small active length (when the handle 58 has been moved to the left in FIG. 7) and with a comparatively smaller spring constant for a long active length (when the handle 58 has been moved to the right in FIG. 7).

Figure 8:
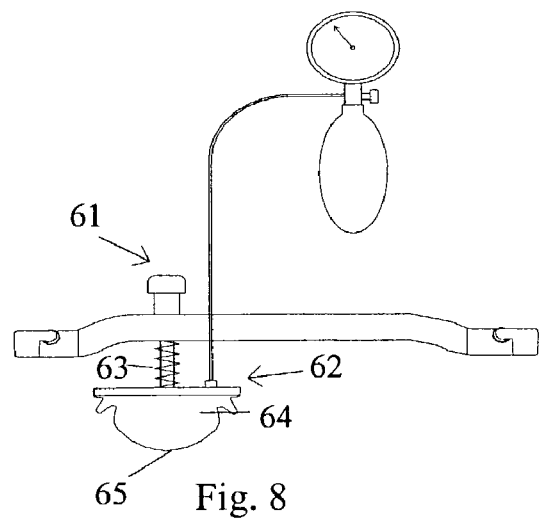
FIG. 8 illustrates a fifth embodiment of a pressure device according to the present invention.

As mentioned above, the principles of the invention are not restricted to a mechanical pressure device, such as coil or leaf springs, but are equally applicable to other types of pressure device(s). In FIG. 8 an arrangement is shown, where a femoral compression device 61 is provided with a pressure device 62 which comprises a coil spring 63 and an inflatable air cushion 64, whose lower portion constitutes a compression member 65 adapted for compressive bearing at a puncture site. By choosing a coil spring 63 being characterized by a suitable spring constant and an inflatable air cushion 64 being characterized by a suitable action constant, the pressure device 62 can be provided with an overall action with which it is possible to obtain a small action constant when a low compression pressure is required and a large action constant when a high compression pressure is required.

Although the present invention has been described with reference to specific embodiments, also shown in the appended drawings, it will be apparent for those skilled in the art that many variations and modifications can be done within the scope of the invention as described in the specification and defined with reference to the following claims. For example, the invention can be applied to compression devices for other arteries or vessels.

What is claimed is:

1. A compression device adapted to be arranged at the body of a patient and for compressing a vessel, comprising
a base plate, connected to two extensions which proceed outward from the base plate in opposite directions, each of the extensions having at an end away from the base plate a device configured to retain a belt to secure the compression device to a patient with the belt,
a pressure device, and
a compression member, which receives pressure from the pressure device, configured for compressive bearing against a puncture site of the patient,
wherein the pressure device has at least a first portion having a first action constant and a second portion having a second action constant, the first portion and the second portion being two physically distinct portions of the pressure device, the second action constant being higher than the first action constant, wherein the pressure device is operatively connected between the base plate and the compression member and is characterized by a non-uniform overall action constant over the operating range of the pressure device, such that when a low compression pressure is applied, the pressure device exhibits a small action constant over a portion of the operating range of the pressure device, and when a high compression pressure is applied, the pressure device exhibits a large action constant over another portion of the operating range of the pressure device, wherein the pressure device does not include said device, of each extension, that is configured to retain the belt and does not include the belt, and wherein the pressure device comprises a mechanical pressure device and a pneumatic pressure device.

2. A compression device adapted to be arranged at the body of a patient and for compressing a vessel, comprising
a base plate,
a pressure device, and a compression member, which receives pressure from the pressure device, for compressive bearing against a puncture site, wherein the pressure device is operatively connected between the base plate and the compression member and is characterized by non-uniform overall action constant over the operating range of the pressure device, such that when a low compression pressure is applied, the pressure device exhibits a small action constant over a portion of the operating range of the pressure device, and when a high compression pressure is applied, the pressure device exhibits a large action constant over another portion of the operating range of the pressure device, wherein the pressure device comprises mechanical pressure means and a pneumatic pressure means, wherein the mechanical pressure means comprises at least one spring.

3. A compression device according to claim 1, wherein the pneumatic pressure device comprises an inflatable air cushion.

4. A compression device according to claim 2, wherein the at least one spring is provided between the pneumatic pressure means and a handle, which can be operated to adjust the compression of the spring.

5. A compression device according to claim 1, wherein the compression member is configured for compressive bearing against a puncture site in a femoral artery.

6. A compression device adapted to be arranged at the body of a patient and for compressing a vessel, comprising a base plate, connected to two extensions which proceed outward from the base plate in opposite directions, each of the extensions having at an end away from the base plate a device configured to retain a belt to secure the compression device to a patient with a belt, a pressure device, and a compression member, which receives pressure from the pressure device, configured for compressive bearing against a puncture site of the patient, wherein the pressure device has at least a first portion having a first action constant and second portion having a second action constant, the first portion and the second portion being two physically distinct portions of the pressure device, the second action constant being higher than the first action constant, wherein the pressure device is operatively connected between the base plate and the compression member and is characterized by a non-uniform overall action constant over the operating range of the pressure device, such that when a low compression pressure is applied, the pressure device exhibits a small action constant over a portion of the operating range of the pressure device, and when a high compression pressure is applied, the pressure device exhibits a large action constant over another portion of the operating range of the pressure device, wherein the pressure device does not include said device, of each extension, that is configured to retain the belt and does not include the belt, wherein the pressure device comprises a spring and an inflatable cushion.

* * * * *